United States Patent [19]

Tiollais et al.

[11] Patent Number: 5,591,638
[45] Date of Patent: Jan. 7, 1997

[54] METHOD FOR THE TRANSFORMATION OF CELLS, PARTICULARLY EUKARYOTES BY A DNA ORIGINATING FROM VIRUSES OF HEPATITIS, MORE PARTICULARLY FROM VIRUS OF B VIRAL HEPATITIS, AND PREPARATIONS CONTAINING THE EXPRESSION PRODUCTS OF SAID DNAS

[75] Inventors: Pierre Tiollais; Charles Chany, both of Paris; Marie-Françoise Dubois, Versailles; Christine Pourcel; Anne Louise, both of Paris, all of France

[73] Assignee: Institut Pasteur and Institut Nationale de la Sante et de la Recherche Medicale, Paris, France

[21] Appl. No.: 191,133

[22] Filed: Jan. 25, 1994

Related U.S. Application Data

[60] Continuation of Ser. No. 900,483, Jun. 18, 1992, abandoned, which is a division of Ser. No. 482,322, Apr. 5, 1983, Pat. No. 5,314,808, which is a continuation of Ser. No. 256,126, Apr. 21, 1981, abandoned.

[30] Foreign Application Priority Data

Apr. 22, 1980 [FR] France .................................. 80 09041
Dec. 9, 1980 [FR] France .................................. 80 26132

[51] Int. Cl.$^6$ .......................... C12N 15/51; C07H 21/04; C12Q 1/70
[52] U.S. Cl. .................. 435/320.1; 435/5; 435/69.3; 435/172.3; 435/240.2; 536/23.72
[58] Field of Search ........................... 435/5, 69.3, 172.3, 435/240.2, 320.1; 536/23.72

[56] References Cited

U.S. PATENT DOCUMENTS

| | | |
|---|---|---|
| 4,088,746 | 5/1978 | McAleer et al. . |
| 4,181,713 | 12/1979 | McAleer et al. . |
| 4,186,193 | 1/1980 | McAleer et al. . |
| 4,741,901 | 4/1984 | Levinson et al. . |
| 4,769,238 | 9/1988 | Rutter et al. . |
| 4,775,622 | 10/1988 | Hitzeman et al. . |
| 4,935,235 | 6/1990 | Rutter et al. ................................ 424/88 |
| 5,024,938 | 6/1991 | Nozaki et al. ........................ 435/68.1 |

FOREIGN PATENT DOCUMENTS

| | | |
|---|---|---|
| 1169793 | 6/1984 | Canada . |
| 0013828 | 6/1980 | European Pat. Off. . |
| 0020251 | 10/1980 | European Pat. Off. . |
| 0177015-AZ | 4/1986 | European Pat. Off. ....... A61K 39/29 |
| 2034323 | 4/1980 | United Kingdom . |

OTHER PUBLICATIONS

Dubois et al., "Excretion of hepatitis B surface antigen particles...," Proc. Natl. Acad. Sci. 77:4549–4553 (1980).
Hirschmann et al., Proc. Natl. Acad. Sci 77 5507–5511 (1980).
Colbore–Garapin et al., Proc. Natl. Acad. Sci. 76:3755–3759 (1979).
Wialer et al., Cell 16:777–785 (1980).
Gavilanes et al., J. Biol. Chem. 257:7770–7777 (1982).
Garety et al., J. Infec. Dis. 140:642–648 (1979).
Peterson, J. Biol. Chem. 256:6975–6983 (1981).
Lai et al., Proc. Nat'l Acad. Sci. 77:244–248 (1980).
Tiollais et al., Scientific American, Apr. 1991, 116–123.
DuBois et al., PNAS 77:4549–4553 (1980).
Charnay et al., Nature 286:893–895 (1980).
Charnay et al., PNAS 76:2222–2226 (1979).
Valenzuela et al., Nature 280:815–819 (1979).
Galibert et al., Chem. Abstr. 96:408752 (1982).
Galibert et al., Abstract of French patent (Mar. 6, 1981).
Siddiqui et al., PNAS 76:4664–4668 (1979).
Fritch et al., C.R. Acad. Sci. Paris Ser. D 287:1453 et. seq. (1978).
Sninsky et al., Nature 279:346–349 (1979).
Galibert et al., Nature 281:646–650 (1979).
Summers et al., PNAS 72:4597–4601 (1975).
Burrell et al., Nature 279:43–47 (1979).
Peterson et al., PNAS 74:1530–1534 (1977).
Skelly et al., Nature 282:617–618 (1979).
Aden et al., Nature 282:615–616 (1979).
Robinson et al., N. Engl. J. Med. 295:1168–75 (1976).
Robinson et al., N. Engl. J. Med. 295:1232–36 (1976).
McAuliffe et al., Rev. Infect. Dis. 2:470–492 (1980).
Zuckerman, Nature 255:104–105 (1975).
Zuckerman, The Lancet, pp. 1396–7 (Jun. 26, 1976).
Purcell et al., Am. J. Med. Sci. 270:395–399 (1975).
Cohen et al., Nature 296:677–8 (1982).
Edman et al., Nature 291:503–506 (1981).
Pasek et al., Nature 282:575–579.

*Primary Examiner*—Michael P. Woodward
*Attorney, Agent, or Firm*—Finnegan, Henderson, Farabow, Garrett & Dunner, L.L.P.

[57] ABSTRACT

Method for the production of antigens vaccinating against the virus of B viral hepatitis. It consists of transforming a cell culture with a vector, more particularly a plasmid, itself containing an insertion sequence including itself at least the part of the viral DNA coding for the immunogen protein, capable of inducing in vivo antibody production active with respect to the whole virus, as well as the viral promoter under the control of which the transcription and translation of the above-said part of viral DNA is normally carried out, in particular in a host infected with the corresponding virus.

1 Claim, 1 Drawing Sheet

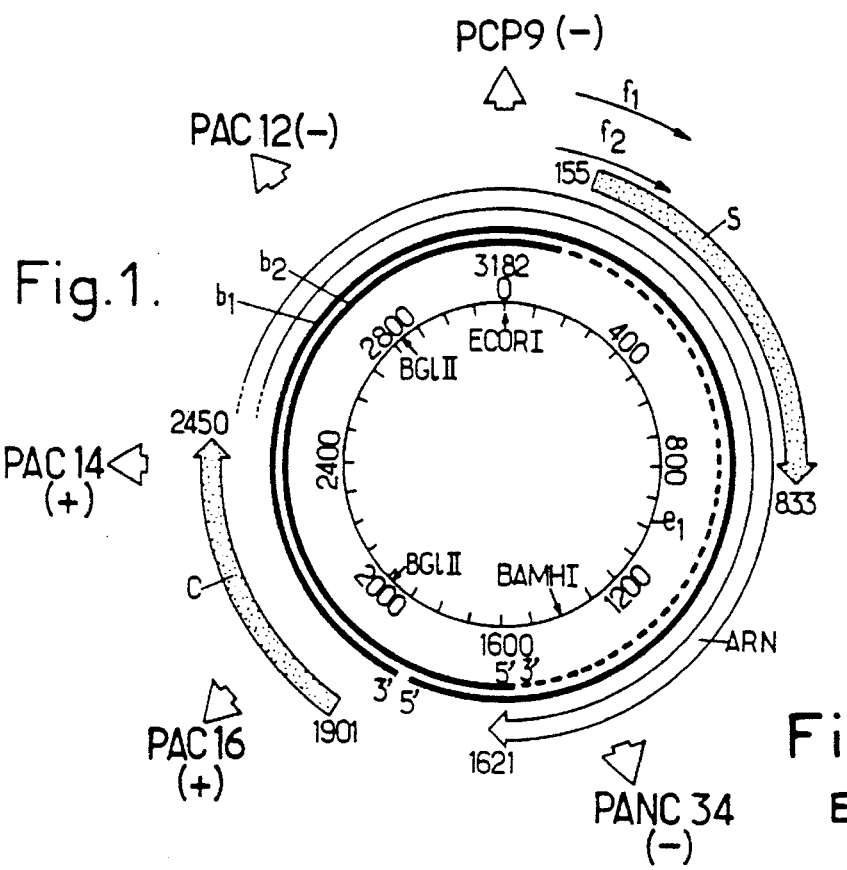
Fig. 1.
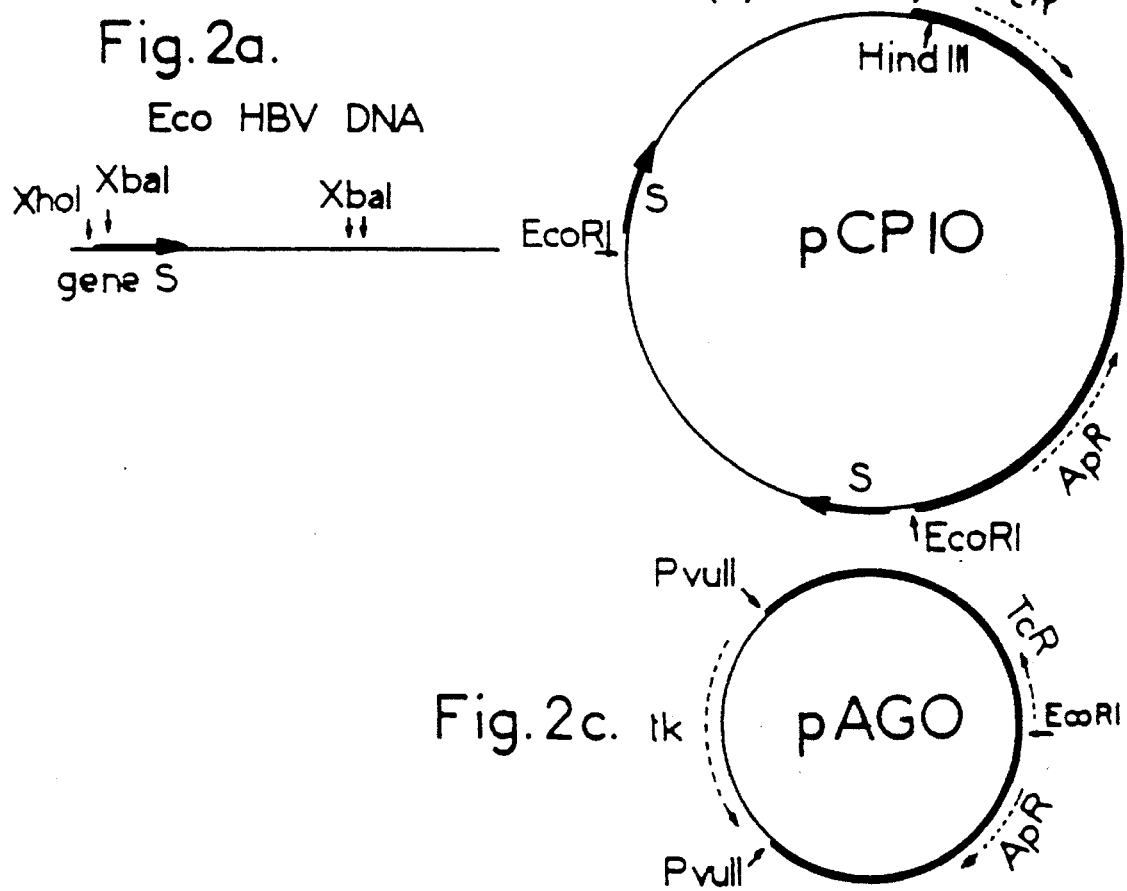
Fig. 2a. Eco HBV DNA
Fig. 2b. pCP10
Fig. 2c. pAGO

METHOD FOR THE TRANSFORMATION OF CELLS, PARTICULARLY EUKARYOTES BY A DNA ORIGINATING FROM VIRUSES OF HEPATITIS, MORE PARTICULARLY FROM VIRUS OF B VIRAL HEPATITIS, AND PREPARATIONS CONTAINING THE EXPRESSION PRODUCTS OF SAID DNAS

This application is a continuation of application Ser. No. 07/900,483, filed Jun. 18, 1992, now abandoned which is a division of application Ser. No. 06/482,322, filed Apr. 5, 1983, now U.S. Pat. No. 5,314,808 which is a continuation of application Ser. No. 06/256,126, filed Apr. 21, 1981 now abandoned.

BACKGROUND OF THE INVENTION

1. Field of the Invention

The invention relates to a preparation containing antigens possessing immunological properties, notably antigenic properties, characteristic of viruses of various forms of hepatitis, such as B viral hepatitis or various other forms of hepatitis such a those which are known to be developed in certain patients following blood transfusions, for example hepatitides called "non A" or "non B". The invention relates more particularly to preparations of this type, which are characterised by high purity, the absence of proteins of human origin and, when it concerns preparations having antigen properties similar to those of the HBs antigens, free of Dane particles. It also relates to a method for the production of these antigens.

2. Description of the Prior Art

It is known that certain of the specific antigen properties of the virus of hepatitis must be attributed to an antigen called "HBs Antigen" or "HBsAg", essentially formed by the envelope of the virus of viral hepatitis of the B type (HBV) or Dane particle. This antigen, which possesses vaccinating properties with respect to type B viral hepatitis, is, at the present time, essentially obtained from human serum specimens. However, no other sources for the supply of HBsAg, are by now available by reason of the particular characteristics of the virus of B hepatitis (HBV). It seems only capable of infecting man, the chimpanzee and, perhaps, a small number of other primates. It has not been possible hitherto to propagate it in vitro in cell cultures. Certain lines of hepatocarcinomas which synthesize HBsAg are known. The use in man of cancerous cells for the production of particles with a vaccinating character runs up against quite comprehensible objections. The use in preventive therapy of HBs antigens of human origin is not however devoid of serious risks. In fact, they arise generally from persons who have been exposed to the virus of B viral hepatitis, so that the presence of Dane particles, sometimes also highly infectious, in preparations of HBsAg antigens of serum origin cannot always be completely excluded, even in the case of extremely pure preparations. The contents of the even highly purified preparations of HBsAg antigen from the state of the art in serum proteins or other possibly antigenic components, capable of inducing in the treated subjects troublesome immunological reactions, are not negligible, by reason of their very low initial content of HBsAg with respect to the proteins of the initial serum (for example, of the order of 50 μg of HBsAg with respect to 80 mg of protein in a 1 ml of serum).

In spite of the difficulties encountered to have available sufficient amounts of virus, it has however been established that the genome of the virus of B hepatitis is formed from a partially single stranded circular DNA molecule, of which the longest strand includes of the order of 3200 nucleotides (SUMMERS J. and coll. (1975) Proc. Nat. Sci. U.S.A. 72, 4597–4601). At the most, it has been possible to localise the gene coding the portion of the protein of the HBsAg antigen, which is responsible for the immunological properties of the envelope of the virus of B hepatitis. The position of this gene, named "S gene" results notably from the diagrammatic map of the genome of the Dane particle, which is given in FIG. 1 of the drawings.

FIG. 1 comprises a diagrammatic map of the DNA of the genome of the Dane particle. This DNA comprises two strands $b_1$ and $b_2$, the shortest of them ($b_2$) being normally devoid of the portion shown by a dashed line in the drawing.

It is known that this DNA only includes a single EcoRI site.

The arrow $f_1$ gives the direction of the numbering of the nucleotides from which the longest strand $b_1$ is composed, and the arrow $f_2$ gives the direction of the transcription of the S gene by the cellular machinery of the cells invaded by the virus of B hepatitis.

The EcoRI site can hence be numbered 0, or 3182 (in the case of B hepatitis viruses belonging to serotype 3182) (NATURE, 1979, vol. 281, p. 646–650).

The inner concentric circle $e_1$ gives the scale in numbers of nucleotides. This circle enables the positions of certain of the parts of this DNA to be specified. The numbers 3', 5' and 5', 3', at the lower part of the map indicate the terminal ends bearing the same numbers in conventional representations of the ends of the nucleic acid chains.

At the most, the coding gene for the part of the protein of the HBsAg antigen has been localised. The position of this gene, named "S gene", is shown diagrammatically by the arrow S in the Figure. The "S gene" is essentially borne by the fragment of the longest strand $b_1$ situated between the nucleotide positions 155 and 833 of the diagrammatic map of FIG. 1 in the direction of the transcription of the S gene.

The shortest strand ($b_2$) of the genome of the Dane particle can be "repaired" in vitro in the presence of precursor nucleotides and of a polymerase, for example by the technique of T. A. LANDERS and coll., J. VIROL., 23, 1977, p. 368–376. The genomes so-repaired of the viral hepatitis viruses (or any DNA capable of coding for the same aminoacid sequences) will be denoted below by the abbreviation DNA HBV.

It is therefore an object of the invention to provide processes such as have been specified above, which are applicable generally to the study and to the expression in eukaryotic cells of all or part of the whole genomes of the viruses responsible for the various viral hepatites, more particularly of DNA HBV. It is also an object to provide for the production of modified vectors enabling the practising of these methods.

Lastly, it is more particularly an object of the invention to provide for the production of preparations containing antigens having the same immunological specificity as HBsAg or of a similar antigen of high purity, as has been indicated above, from a system other than human serum, which system is both reproducible and stable (or having a certain number of particular characteristics which can be made the subject of constant surveillance).

SUMMARY OF THE INVENTION

According to the invention there is provided a method for determining the eventual possibility of transformation of a culture of particular cells by a DNA normally circular or a whole genome of the corresponding virus, which method comprises the operation which consists of transforming this cell culture with a vector, more particularly a plasmid, itself containing an insertion sequence including itself at least the portion of the viral DNA coding for the immunogenic protein, capable of inducing in vivo the production of active antibodies with respect to the whole virus, as well as the viral promoter under the control of which the transcription and the translation of the above-said portion of viral DNA is normally carried out, in particular in a host infected by the corresponding virus.

According to a first embodiment of the invention, the above-said insertion sequence is formed by at least two of these DNAs, such as two DNA HBVs, oriented in the same direction of transcription and in which the tail of one is connected to the head of the other. In the following, there will often be used, for convenience of language, the expression "tandem sequence", to denote insertion sequences comprising two DNAs of the type concerned, except when otherwise specified.

In a preferred embodiment of the method according to the invention, the above-said insertion sequence is formed from at least two of these DNA HBVs or from two fragments of DNA HBV, normally contained in DNA HBV on each side of its EcoRI site, oriented in the same direction of transcription, one of these fragments of DNA HBV containing the sequence of nucleotides of the S gene, which is adapted to code for the polypeptide responsible for the immunological properties of the HBs antigen and the other of said fragments being sufficiently long for it to be capable of including the promoter of the S gene.

According to a first preferred embodiment of the process according to the invention, the oriented DNAs of the insertion sequence are constituted by fragments of DNA HBV, the tail of one of these fragments being connected to the head of the other fragment at the level of an EcoRI site.

It is self-evident that certain non essential parts of the latter insertion sequences can be deleted. Such an insertion sequence contains therefore advantageously, on the one hand, the DNA HBV fragment which contains the nucleotide sequence of the S gene, coding for the polypeptide responsible for the immunological properties of the HBs antigen and, on the other hand, a DNA HBV fragment being sufficiently long for it to be capable of including the promoter of the S gene, upstream of the preceding fragment in the direction of transcription these two fragments being normally situated on each side of the DNA HBV EcoRI site.

In other words, this insertion sequence comprises notably, if one refers to FIG. 1, on the one hand, the sub-fragment comprised between the nucleotide positions 833 to 0 (direction reverse to $f_1$), when this sub-fragment comprises the S gene as a whole and, on the other hand, a sub-fragment comprised between the position 3182 and a position corresponding to a number sufficiently distant from this 0 position, in the reverse direction of the transcription, so that the above-said promoter can be included therein.

It is observed that the last sub-fragment must normally comprise a TATATAA sequence, which is normally found upstream of the beginning of the S gene, at a distance corresponding to a number of nucleotides of the order of 235. More particularly again, the insertion sequence will comprise an additional portion of the DNA HBV situated upstream of the BglII site, itself at the level of the nucleotide 2840.

According to an additional feature of the invention, the insertion sequence comprises also in addition a sub-fragment downstream of the S gene in the direction of transcription, this fragment extending normally in the direction of the transcription beyond the DNA HBV BamHI site.

A preferred insertion sequence comprises the whole of the coding gene for the messenger RNA corresponding to the HBs antigen. The relative position of this RNA messenger is represented in FIG. 1 by the arrow ARN of which the beginning coincides substantially with the position of the nucleotide 2800, of one refers to the map of FIG. 1, and which terminates between the BamH$_1$ and BGlII 1986 site.

A preferred insertion sequence capable of being applied in the method according to the invention is hence characterised in that it comprises both the S gene and the coding gene for the messenger RNA corresponding to the HBs antigen. As is to be concluded from the rest of this description, this sequence is preferably devoid of any part of the coding gene for the HBc antigen, sufficing to be expressed in the form of a protein having the immunogenic properties of the HBc antigen.

In the rest of this description, reference will be made more particularly to DNA HBV. It is nonetheless understood that all the techniques which are described are also applicable to the DNA or corresponding whole genomes of other viruses, responsible for other types of hepatitis.

Preferably, conditions are adopted which permit at the same time labelling of the transformed cells, so as to render their detection easy, for example, by using cells or mutants of these cells rendered deficient, for selection purposes (natural or induced deficiency), of a selectable labelling gene normally necessary for their growth, when they are placed in certain particular culture media, these cells being nevertheless capable of developing again in one at least of these same culture media, after introduction in these cells of a gene or fragment of homologous DNA, although of foreign origin (complementation DNA), capable of compensating or "complementing" said deficiency, the method consisting then, either of attempting to carry out the transformation of said cells:

- either with a single vector containing, on the one hand, the insertion sequence studied, notably derived from DNA HBV, and on the other hand, such a "complementation DNA", respectively inserted in its own genome,
- or with two vectors (simultaneous transformations, or co-transformation),
- one of the vectors, preferably a plasmid, having previously been modified by the insertion in its genome of such a complementation DNA;
- the other vector, preferably also a plasmid, having previously been modified by the insertion in its genome of the abovesaid insertion sequence,
- and of collecting, after their cultivation in the above-defined medium, of the colonies which both developed and which were transformed by the insertion sequence.

To the extent that the DNA HBV is capable of being expressed in the cell of said culture, the tandem sequence (or containing more than two DNA HBV units), or more generally the insertion sequence such as has been defined above, must normally behave as would the corresponding circular DNA thus introduced into the cell, in the absence of any vector.

The use of such a vector, notably a plasmid, instead and in place of the circular DNA itself is of very great interest in that it is possible to have considerable amounts of such a vector after amplification of the vector previously constructed in vitro by cloning in bacteria.

The process according to the invention hence permits testing the capacity of a circular DNA or of a whole virus genome—in particular DNAs of hepatitis viruses other than DNA HBV—to be expressed in eukaryotic cells, to be tested, without it being necessary to give regard to the exact position of the promoter under the control of which the transcription is to be effected.

The vectors modified by the above-said insertion sequences, notably those derived from DNA HBV can be used to induce the expression of these insertion sequences in eukaryotic cell cultures, notably of the mouse or of human origin.

When there is used, for the labelling of transformed cells, a distinct vector, notably a plasmid containing the marker, it is preferable to resort to a plasmid containing a "complementation DNA", such as the gene of thymidine-kinase of the Herpes simplex HSV-1 virus, which can be excised from the genome of the virus by specific enzymes restrictions such as BamHI. To this gene of thymidine-kinase of viral origin correspond, in numerous types of eukaryotic cells, homologous genes adapted to direct the synthesis of the thymidine-kinase (enzyme phosphorylating the exogenous thymidine supplied by the culture medium).

The possiblity of overcoming certain genetic deficiencies of eukariotic cells, notably of the mouse, for example, those relating to their gene of endogenous thymidine-kinase, by reason of an induced or provoked mutation, has already been described by M. WIGLER and coll. (Cell vol. II, 223–232, 1977). The deficient cells, called TK$^-$, are selected by reason of their incapacity to synthesize thymidine kinase in a medium such as that known by the name "HAT medium-"(containing hypoxanthine and aminopterine in addition to thymidine). This medium is known for only permitting the possible synthesis of thymidine phosphate via a metabolic route called "salvation pathway", this route implies however that the integrity of the TK gene of the cells capable of being developed therein be preserved. TK$^-$ cells become nonetheless capable of development in this same medium as soon as they have been modified by incorporation of the TK gene of the virus of the herpes which is then genetically transmissible to their descendants, as a result of successive cell divisions. From "TK$^-$" as they were previously, before the abovesaid incorporation, these cells have then become "TK$^+$", due to the fact of the restoration then observed of their capacity to phosphorylate thymidine in the abovesaid medium and consequently of developing therein.

Of course, the DNA fragment containing the gene of thymidine kinase can be replaced by any other suitable complementation DNA. By way of example of other complementation genes which can be used for the constitution of the vectors according to the invention, will be mentioned that containing that of dihydrofolate reductase (DHFR), or in general, any complementation gene of which numerous examples exist in nature.

The complementation DNA may naturally include a natural gene. It may also be synthesized, notably enzymatically, by copying a corresponding messenger RNA.

As regards the technique of co-transformation itself, it is advantageous to use the vector in which the complementation gene is inserted and the vector in which the derived DNA HBV fragment is inserted in amounts that are in a high ratio above 100, for example of the order of 1000. The higher this ratio, the greater then the number of cells co-transformed by the two vectors at the same time.

It is advantageous to resort to the same basic vectors to form the two types of modified vectors used for the co-transformation. A particularly favorable basic vector is constituted by the plasmid pBR322. It will be possible in particular to insert a "DNA HBV tandem" into its EcoRI site to form one of the modified co-transformation vectors (pCP10).

By the insertion of a tkHSV gene, either into a PvuII site, or into a BamHI site of the same pBR322 plasmid, it is possible to obtain the second co-transformation vector (pAG0).

As regards the cultivation conditions, it is naturally self-evident that the medium previously used to reach a sufficient development of the cultures, must be replaced at the time of the transformations a little thereafter by a medium such as the HAT medium in the case where the complementation DNA selected is a thymidine-kinase gene, in which the non-complemented cells are incapable of developing.

The production of the co-transformations, particularly when the above-said preferred modified plasmids are used in mouse fibroblasts, leads to the remarkable result constituted by the secretion of particles having immunological properties characteristic of the envelopes of the hepatitis B virus into the culture medium by the co-transformed cells notably these particles are agglutinated by antibodies capable of agglutinating the natural HBsAg antigens, as isolated from human serum. The presence of secreted particles agglutinatable by anti-HBsAg antibodies can be detected by conventional radio-immunological tests, for example by indirect immunofluorescence using fluorescent anti-HBsAg and anti-IgG rabbit serum.

The amount formed can be measured by direct passive hemagglutination tests, in manner known in itself for natural HBsAg.

It is also remarkable that the secreting cells, notably in mouse cell cultures, do not contain detectable traces of HBcAg and HBeAg antigens, detectable by direct immunoflurorescence using fluorescent human antibodies anti-HBc and anti HBe/1, 2, 3. By contacting the co-transformed cells themselves with an anti-HBsAg serum, individualised cytoplasmic granules are shown by indirect immunofluorescence in a large part of the co-transformed cells. These particles can also be spotted after lysis of the cells. In the majority of cases the secreted particles form the major part of the particles agglutinatable by anti-HBsAg antibodies which can be produced.

The particles formed, whether secreted into the medium or retained in the cytoplasm of the co-transformed cells, still have the properties which will again be mentioned below in the description of the examples.

It was found however that the transformation of HeLa human cells with a circularised cloned DNA of a hepatitis B virus led to the secretion by these cells not only of HBs antigen, but also of complete viral particles containing HBc antigen in the culture medium (9).

Also it is advantageous, according to an additional improvement of the invention, to resort to an insertion sequence such as has been described above, derived from DNA HBV, from which there has previously been excised certain portions external to the S gene of the DNA HBV, so as to use only effective genomes which are no longer capable of coding for whole Dane particles. In particular, recourse is advantageously had to an insertion sequence from which a sufficient portion of the coding gene for the HBc antigen has been deleted, in order to prevent the production of the latter antigen by the infected cells.

These insertion sequences can consequently be used to modify vectors which will then be suitable for transforming eukaryotic cells, whether it relates to mouse fibroblasts or human cells, but in the absence of any possibility of HBc antigen production.

In particular, the DNA insertion is advantageously constituted by the DNA of the virus of viral hepatitis B, from which the fragment bounded by the BglII ends at the level of the nucleotides 1986 and 2425 has been deleted, if reference is made to the diagrammatic map of FIG. 1, inside the C gene, whose relative position with respect to the whole DNA has been symbolised by the C arrow.

It is also possible to resort to original insertion sequences of DNA HBV, from which larger fragments have been deleted. Notably such as already defined above.

Of course, this insertion DNA can comprise additional deletions as long as the latter neither affect the expression capacity of the insertion sequence, nor the phases of its translation. In the same way, the invention extends to the use of any equivalent insertion sequence, whether it relates to the sequence corresponding to a viral DNA belonging to another sub-type than that which has been contemplated in the present description and taken up in the examples, or of a sequence from which certain parts would have been modified without having altered the capacity of the expression products to react immunologically with antibodies against HBs antigens.

It has thus been possible to obtain, from cell cultures of mouse fibroblasts transformed with modified vectors by insertion sequences, such as defined above, antigen preparations having the immunological characteristics of HBsAg antigen, devoid (within the limits of available detection methods) of any Dane particle, and of other characteristic antigens contained in the latter, in the absence of components of human origin, notably of any serum protein.

In addition, it has been verified that the proteins secreted into the culture media in fact posses vaccinating immunogenic properties, as is witnessed by their capacity to induce the production of antibodies in vivo, that are similar to the human anti-HBsAg antibodies and active against hepatitis virus, more particularly B hepatitis, when they are administered in vivo, notably to the mouse or the rabbit, according to currently used experimental procedures to verify the immunogenicity of the natural HBs antigens, extracted from human serums.

The invention hence also relates to novel preparations useful for the constitution of vaccines, characterised in that they consist of proteins having immunogenic and immunological properties characteristic of the HBsAg antigen, having a total purity level as regards the absence of any Dane particle, of HBc antigen and of any serum component of human origin.

The invention relates more particularly to vaccine compositions containing said antigens (such as can be recovered from culture media of said co-transformed cells or from lysates of the latter), if necessary, associated with any suitable pharmaceutical vehicle for the constitution of an active vaccine against viral hepatitis capable of being administered by the oral or parenteral route.

The invention also relates to laboratory reagents containing particular doses of these antigens, capable notably of being used as standards or references with respect to which the degree of purity of preparations containing HBsAg antigens, whether of natural origin or not, can be evaluated as regards in particular their relative content of serum proteins, or other antigens, such as HBcAg or HBeAg, etc.

The invention will again be illustrated by the description of examples of the application of modified plasmids (which themselves form part of the invention) for the manufacture of antigens having immunological properties of HBsAg.

BRIEF DESCRIPTION OF THE DRAWINGS

In this description, reference will again be made to FIG. 1 already mentioned and to FIGS. 2a, 2b and 2c, which represent diagrammatic maps of preferred plasmids which have been utilised according to the invention.

In the description, the numbers between parentheses refer to the bibliography added at the end of this specification.

DETAILED DESCRIPTION OF PREFERRED EMBODIMENTS

EXAMPLE I

Construction of a Recombinant Containing DNA of the Virus of B Viral Hepatitis.

200 ng of pBR322 were subjected to digestion by the endonuclease EcoRI and treated with 2.6 units of alkaline phosphatase in 100 nM of Tris-HCl, pH 8, at 60° C. for 60 minutes. After two extractions with phenol, then three extractions with ether, the DNA was precipitated by ethanol. The solid residue was dissolved in water and added to the solution 100 ng of Eco HBV DNA. The ligation was carried out according to the method described in (1).

A culture of *E. coli* DP 50 followed in a culture medium constituted by a broth L containing 100 µg/ml of diaminopimelic acid and 20 µg/ml of thymidine.

The bacteria were then transformed according to the above-indicated method by mixing recombinants selected according to their capacity of withstanding doses of 100 µg/ml of ampicillin and 15 µg/ml of tetracycline. 900 colonies were obtained. They were all tested by hybridation in situ for the determination of the presence or not of HBV DNA. The test was positive for 800 colonies. The 16 colonies which induced a hybridation signal of higher intensity were collected. The plasmids were extracted and their structure was analysed by digestion in the presence of EcoRI, XhoI, HindIII and XbaI.

The structure of the recombinant obtained results from FIGS. 2a and 2b in which have been shown diagrammatically, one one hand, the structure of the Eco HBV DNA gene and, on the other hand, the structure of the modified pCP10 plasmid, and such as results from the insertion in the plasmid pBR322 of a DNA fragment constituted by two successive Eco HBV DNA fragments, the head of one being connected to the tail of the other, at the level of an EcoRI site (insertion in tandem head to tail).

It is observed that among the 16 above colonies which were retained, 14 among them harbored plasmids of the pCP10 type, in which the two Eco HBV DNA occured inserted according to the head to tail tandem arrangement in the two directions of orientation possible.

It is in particular due to the digestions with HindIII and XbaI endonucleases that it has been possible to determine the insertion directions of the Eco HBV DNA fragments Eco.

The integrations in the pCP10 plasmid of two Eco HBV DNA fragments were demonstrated by digestion in the presence of XhoI endonuclease, which produce the excision of an DNA fragment having a size similar to that of Eco HBV DNA from the hybrid plasmid pCP10. The latter includes 10,626 pairs of bases.

The respective positions of the S gene in Eco HBV DNA (FIGS. 2a and 2b) and in the hybrid plasmid pCP10 are respectively represented by the arrows S drawn in heavy lines. The small side arrows locate the relative positions of certain of the restriction sites in the corresponding DNA chains. The positions of the resistance factors to ampicillin ($Ap^R$) and to tetracycline ($Tc^R$) are also shown diagrammatically.

The same conventions apply to the pAG0 plasmid (FIG. 2c) which has been obtained by insertion into the PvuII site of the pBR322 plasmid of the gene of thymidine-kinase of the Herpes simplex virus HSV-1 (HSV-tk) (2).

Cultivation and Transformation by the above-said Plasmids of Thymidine-Kinase Deficient Mouse Cells (Ltk$^+$).

Mutants of LM mouse cells deficient in thymidine-kinase (Ltk$^-$) were cultivated in the minimum essential medium MEM 0 111 Gibco, if necessary in the presence of 10% calf serum. Confluent monolayers of these cells ($2 \times 10^6$ cells per 24 cm$^2$) in Falcon flasks were inoculated for their transformation with DNAs corresponding to the plasmids, according to the method of GRAHAM and VAN DER EB (3) as modified by STOW and WILKIE (4).

To carry out this transformation there was used at the same time the pAG0 plasmid (linearised by HindIII endonuclease) and pCP10 plasmid linearised or not by the same enzyme. In all the tests the molecular ratio pAG0/pCP 10 has been of the order of 1/1,000. DNA salmon sperm was used as a vehicle to adjust the concentration of DNA to at least 10 µg/ml.

After the transformation, the cell cultures were kept in this medium containing in addition 15 µg/ml hypoxanthine, 0.1 µg/ml of aminopterine and 5 µg/ml of thymidine (selective HAT medium).

24 hours after the transformation, there was added to the medium a HAT solution concentrated 100 times. The concentrated solution was changed a week later, and then every three days.

After 15 days of cultivation in the presence of the two types of plasmids (co-transformation) in the selective HAT medium, the formation of colonies was observed. 20 days after the co-transformation, the HBsAg production was detected in the culture medium by radio-immunological tests. Cultures formed under the same conditions and transformed for purposes of comparison with the single plasmid pAG0 did not induce any HBsAg production.

The tk$^+$ colonies resistant to the HAT medium were collected with a Pasteur pipette (20 days after the co-transformation) and transferred to tissue culture on microplates. Passages of the colonies were carried out every 5 days and they were maintained under continuous selective pressure in the HAT culture medium.

Five of these colonies obtained from co-transformation in the presence of linearised pCP10 and 10 colonies obtained from the co-transformation of the mouse cells with the circular pCP10 were sampled and cultivated in HAT medium. All the cultures produced HBsAg which was released in the external culture medium.

The amounts of HBsAg synthesized were variable from one culture to the next (within limits in a ratio 1 to 30). The amounts produced were stable, even after several passages of said cultures.

The HBsAg can be recovered by centrifugation of the supernatant liquor of the cultures and purified by centrifugation in a density gradient based on CsCl. The HBsAg were collected in the zone of density 1.20 g/ml. These HBsAg were completely neutralised by an anti-HBsAg serum solution (in a ratio 10/1), after incubation at 37° C. for one hour, as detected by radioimmunology tests.

On examination under the electron microscope, spherical particles were observed having sizes ranging from 18 to 25 nm (on the average 22 nm). Their morphology recalled that of the spherical particles of antigens of 22 nm which can be isolated from human serum. Filamentous structures such as those visible among the antigens extractable from human serum have not been observed, at least under the conditions of the experiment. No Dane particle was detected.

The following Table illustrates the production capacity of the mouse cells tk$^-$ which had been co-transformed by the plasmids concerned.

The ratio P/N corresponds to the ratio of the number of disintegrations per minute (dpm) measured on the supernatant liquor to the number of dpm measured on a controlled culture when the dosages of HBsAg were done by immunological tests 20 days after the co-transformation of the cells. A ratio P/N higher than 2.1 was considered as significant.

TABLE

Co-transformation of Ltk$^-$ cells of mice with pCP 10 and pAGO plasmids.

| Flask | linearised pAGO | linearised pCP 10 | circular pCP 10 | salmon sperm DNA | number of colonies tk$^+$ | P/N |
|---|---|---|---|---|---|---|
| b | 0.010 | 10 | — | — | 140 | 24 |
| c | 0.005 | — | 5 | 15 | 200 | 16 |
| f | 0.010 | — | — | 15 | 26 | 1 |

After lysis of the previously washed cells, digestion of the proteins in the presence of proteinase, extraction and purification of the cellular DNA, estimation of the cellular DNA by the technique of SOUTHERN modified by WAHL et al. (5, 6) by using a probe Eco HBV DNA prepared by the technique of WEINSTOK et al. (7). It has been observed that the amount of intracellular HBsAg which had been synthetisized approximately corresponds to a third of the HBsAg which had been excreted into the culture medium.

Under the conditions of the experiment, the most active clones produced up to 150 ng/ml of HBsAg.

In addition to the absence already mentioned of Dane particles, no HBcAg and HBeAg antigens were observed at least at a level detectable by direct immunofluorescence utilising anti-HBc and anti-HBe/1,2,3 fluorescent antibodies of human origin (8). Moreover, the production of DNA-polymerase, by measurement of the DNA-polymerase activity by the method of KAPLAN et al., has not been observed (either in the centrifugation residue from the supernatant liquor or in that of the lysate of the previously transformed cells).

By extraction of the DNAs of high molecular weight of certain cloned products, digestion of these DNAs in the presence of EcoRI, Hind III and XhoI, fractionation of the fragments obtained by electrophoresis on agarose gel, transfer to nitrocellulose filters, hybridation of these fragments with Eco HBV DNA probes labelled with phosphorus 32, it has been established that several copies of the plasmid pCP10 could be incorporated into the cellular DNA. There has also been noted the presence of HBV DNA dimers both in the plasmid copies contained in the transformed cells and among the fragments possibly incorporated into the cellular DNAs.

It has also been determined by means of kinetic studies that under the experimental conditions which have been described, HBsAg antigen particles can be secreted into the medium by the cells, in the proportion of $2\times10^4$ to $4\times10^4$ particles/cells/24 hours, namely 2,000,000 to 4,000,000 molecules of polypeptide/cells/24 hours, if it is assumed that each particle contains about 100 molecules of polypeptides.

EXAMPLE II

Expression in Eukaryotic Cells of Vectors Modified by an Insertion Sequence Derived from DNA HBV, from which the Major Portion of the C Gene has Previously Been Excised.

1) Cloning of pCP9 (Resulting From the Insertion of the Linearised pBR322 Plasmid in the EcoRI Site of DNA HBV).

Plasmid pBR322 hydrolysed by EcoRI was treated with alkaline phosphatase, then ligated in the presence of an equimolecular amount of DNA HBV cut by EcoRI. The arrow pCP9 symbolises, in FIG. 1, the insertion site of pBR322 into the DNA HBV.

2) Construction of Clones of the PAC Series (Containing DNA HBV Fragments (Cut by BglII) and PANC (Containing Fragments of DNA HBV cut by BamHI).

The pAG0 plasmid was hydrolysed by BamHI and treated with alkaline phosphatase.

The HBV fragments were obtained from plasmid pCP10 described above, after cleavage by Hind III and Pst I (which have no site in the DNA HBV), and more particularly, from the fragments obtained purified by electroelution of an agarose gel, and containing a dimer—or a "tandem" sequence—of DNA HBV. These fragments were partially hydrolysed, either by the restriction enzyme BglII, or by the BamHI enzyme, under the conditions where only two cleavages were made. The hydrolysates were then ligated in equimolecular amount with pAG0 plasmid previously cleaved by BamHI. This takes advantage of the fact that the BamHI and BglII sites are characterised by common cohesive end portions.

A collection of clones sensitive to tetracycline was obtained and analysed in order to isolate each insertion possibility.

Clones PAC 12, PAC 14, PAC 16 and PANC 34 were obtained. The arrows accompanying the corresponding symbols in FIG. 1, locate the insertions of the linearised pBR322 in the BamHI or BglII sites corresponding to the sequences of DNA HBV contained in the recombinant plasmids obtained.

These clones had in addition the following characteristics:
PAC 12: deletion of the BglII fragment 1985–2840;
PAC 14: deletion of the BglII fragment 1986–2425;
PAC 16: insertion of the genome of pBR322 in the 1986 site of the DNA HBV;
PAC 34: it contained the pBR322 genome in the BamHI 1400 site of DNA HBV.

These clones have been used to transform LTK⁻ cells in the proportions of 2 μg of plasmid per $2.10^6$ cells. 4 weeks later, the TK⁺ colonies reached confluence. The culture medium was then analysed for the presence of HBs by applying the above-said radio-immunological tests.

The capacities or non-capacities of the various recombinant plasmids to express the S gene, in the form of HBs antigen secreted into the culture medium, have been expressed respectively in FIG. 1 by the signs "+" and "−".

The expression of the S gene in the clones PAC 14 and PAC 16 and the failure of expression in the clone PAC 12 show that the transcription of the S gene is initiated in viral DNA and more precisely in the restriction fragment BglII 2425–2840. There exists a sequence TATATAA also called "TATATAA Box" situated at 72 nucleotides upstream of the beginning of the "pre-S" region which appears to control the transcription of the S gene.

The fact that no expression was obtained with the PANC 34 clone, under the conditions in which the experiment was carried out, is perhaps connected with the fact that the DNA encoding for the mRNA stops after the BamHI site.

It is particularly most significant that the PAC 14 clone, which produces the HBs, possesses a deletion in the C gene of the virus, which eliminates the risk of the production of viral particles for the transformed cell, whatever its nature, and permits its use for the production of a vaccine.

The invention hence provides a product capable of a purity unattainable hitherto. It relates more particularly to the preparations of protein particles having the immunological properties of HBsAg, essentially free of serum protein. They are totally free of Dane particles detectable by the usual methods of radio-immunological measurement. They are in addition totally free of proteins, notably serum proteins of human origin. They are free of DNA polymerase.

The invention relates also again to the novel DNA insertion sequences themselves, as they have been defined above, and the vectors, notably plasmids, containing said sequences which are more particularly characterised by the fact that they contain the promoter of the transcription of the S gene. These vectors are of very particular interest in that they can if necessary be modified by the insertion of a particular DNA sequence corresponding to a protein whose expression into eukaryotic cells is sought. In fact, this vector has a particular interest in not being toxic with respect to the cells concerned. The promoter is not repressed, since these cells permit the expression of the S gene. In addition, this vector can enable the secretion of proteins synthesized directly in the culture medium.

One of the above-said novel insertion sequences can again be defined as containing, in addition to the S gene, the DNA of the "pre-S" region (which in the DNA of the virus of viral hepatitis is situated immediately upstream of the S gene in the reverse direction of the transcription, this gene including of the order of 163 nucleotides), the gene of the messenger RNA of the S gene of the virus of B hepatitis, the promoter of the DNA of the virus of B hepatitis, notably a TATATAA sequence (T being abbreviation for thymine and A abbreviation for adenine). It comprises notably also a DNA sequence corresponding to a sequence localised between the nucleotide positions 2425 and 2840 of the DNA of the virus of B hepatitis.

There are obviously included within the scope of the invention, sequences including several units of the above-described type, notably "tandem" sequences.

The capacity of the vectors modified according to the invention of being expressed in eukaryotic cells seems to witness of the fact that the transcription of the gene of HBsAg is under the control of a viral promoter contained in the fragment derived from HBV DNA. These vectors, such as the plasmid pCP 10, PAC 14 or PAC 16, can themselves be used as vectors for effecting the expression in eukaryotic cells of a foreign DNA previously inserted into said vectors. It appears that the advantage of the vectors modified according to the invention must reside in the fact that they do not induce lysis of the host-cells. Moreover the S gene can be considered as having a sequence signal under the control of which the hybrid protein formed, resulting from the expression into the host cells of foreign DNA previously inserted into the above-said vector, would be excreted into the culture medium. The recovery of this hybrid protein would obviously be considerably facilitated therefrom.

Although the method of the invention has been described in the foregoing, principally in its application to DNA HBV, it can be extended to any other circular DNA or whole genomes. In particular it can be applied to the study of circular DNAs of "non A", "non B" viruses of the corresponding viral hepatitides.

Below the bibliography relating to the state of the art and to which reference is made in the description of the examples, is given:

(1) TIOLLAIS, P., PERRICAUDET, M., PETTERSON, U. & PHILIPSON, L. (1976), Gene 1, 49–63.
(2) COLBERE-GARAPIN, F., CHOUSTERMAN, S., HORODNICEANU, F., KOURILSKY, P. & GARAPIN, A. C. (1979), Proc. Natl. Acad. Sci. U.S.A., 76, 3755–3759.
(3) GRAHAM, F. L. & VAN DER EB, A. J. (1973), Virology 52, 456–458.
(4) STOW, N. D. & WILKIE, N. M. (1976), J. Gen. Virol. 33, 447–458.
(5) SOUTHERN, E. M. (1975), J. Mol. Biol. 98, 503–517.
(6) WAHL, G. M., STERN, M. & STARK, G. R. (1979), Proc. Natl. Acad. Sci. U.S.A. 76, 3683–3687.
(7) WEINSTOCK, R., SWEET, R., WEISS, M., CEDAR, H. & AXEL, R. (1978), Proc. Natl. Acad. Sci. U.S.A. 75, 1299–1303.
(8) TREPO, C., HANTZ, L., VITVITSKI, L., CHEVALLIER, P., WILLIAMS, A., LEMAIRE, J. M. & SEPTJIAN, M. (1978) in Viral Hepatitis, eds. VYAS, G. N., COHEN, S. N. & SCHMID, R. (The Franklin Institute Press) pp. 203–209.
(9) SHALOMZ. HIRSCHMAN and Coll., Proc. Natl. Acad. Sci. U.S.A., vol. 77, N°9, pp. 5507–5511, September 1980, "Expression of cloned hepatitis B virus DNA in human cell cultures".

We claim:

1. A recombinant DNA molecule, wherein said recombinant DNA molecule comprises:

more than two Hepatitis B virus (HBV) DNA sequences recombined with a vector, wherein said vector comprises sequences of *E. coli* plasmid pBR322 and has an antibiotic resistance gene as a selective marker, wherein each of said HBV DNA sequences is comprised of full-length HBV DNA, and wherein said HBV DNA sequences are arranged in a head-to-tail tandem relationship.

* * * * *